United States Patent [19]
Spector et al.

[11] Patent Number: 5,608,049
[45] Date of Patent: Mar. 4, 1997

[54] PREPARATION OF D4T FROM 5-METHYLURIDINE

[75] Inventors: Richard H. Spector, Fayetteville; Bang-Chi Chen, East Syracuse; Sandra L. Quinlan, Manlius, all of N.Y.

[73] Assignee: Bristol-Myers Squibb Company, New York, N.Y.

[21] Appl. No.: 402,283

[22] Filed: Mar. 10, 1995

[51] Int. Cl.$^6$ .................................................. C07H 19/073
[52] U.S. Cl. .................. 536/28.2; 536/28.54; 536/27.11
[58] Field of Search ............................... 536/28.2, 28.54, 536/27.11

[56] References Cited

U.S. PATENT DOCUMENTS 3,817,982   6/1974   Verheyden et al. .................. 536/27.14

FOREIGN PATENT DOCUMENTS

0653436A1   5/1995   European Pat. Off. .
5097847     4/1993   Japan .

OTHER PUBLICATIONS

Lehninger, *Biochemistry, Second Edition*, Worth Publishers, Inc., New York, N.Y., 1975, pp. 310, 316 and 321.

Yamaoka et al., "Nucleosides, XLV. 1-α-L-*aldo*-Pentofuranosylpyrimidines," *J. Med. Chem.*, 11(1), 55–59 (1968).

Skaric et al., "Syntheses of β-D-Arabinofurano [1',2': 4, 5] oxa (thia) zolidines," *J. Chem. Soc., Perk Tr.* 1, 1985, 779–783.

Papchikhin et al., "Synthesis of 3'-Azido-and 3'-Amino-3'-deoxyarabinosylnucleoside 5'-Triphosphates and Their Substrate Properties in the System of Polynucleotide Synthesizing Enzymes," *Bioorganich. Khimii*, 11(10), 1367–1379 (1985).

Jones et al., "Di-and Triester Prodrugs of the Varicella-Zoster Antiviral Agent 6-Methoxypurine Arabinoside," *J. Med. Chem.*, 35(1), 56–63 (1992).

Katalenic et al., "Azido-(Amino-) furanosyl Nucleoside and their Phosphoramidates," *J. Chem. Soc. Perk. Tr.* 1, 1992, 1065–1072.

Sasaki et al., "Elimination Reactions on the Di-and Trimesylated Derivatives of N3-Benzyluridine," *J. Organic Chem.*, 38(3), 598–607 (1973).

Sakthivel et al., "One-step Synthesis of C-2 Dialkylamino-substituted 2',3'-O-Anhydro-*lyxo*-uridines: First Report on the Opening of 2, 2'-O-Anhydro-Bridge of 2, 2'-O-Anhydrouridines by Secondary Amines," *Tetrahedron*, 49(45), 10387–10392 (1993).

Classon et al., "A Facile Preparation of 2', 3'-Unsaturated Nucleosides and Hexopyranosides from Acetylated Halohydrins by Reductive Elimination," *Acta Chem. Scand.*, B36, 251–253 (1982).

John F. Codington, Ronald Fecher, and Jack J. Fox, "Nucleosides. XIII. Synthesis of 3'-Amino-3'-deoxy-*arabinosyl*-uracil via 2', 3'-Epoxy-*lyxosyl* Nucleosides", J. Org. Chem., 27, pp. 163–167, Jan., 1962.

Kim L. Dueholm and Eric B. Pedersen, "2,3-Dideoxy-furanoses in Convergent Synthesis of 2'-3'-Dideoxy Nucleosides", Syntheses, pp. 1–22, Jan./Feb. 1992.

P. Herdewijn, J. Balzarini, and E. De Clercq, "2'-3'-Dideoxynucleoside Analogues as Anti-HIV Agents", Advances in Antiviral Drug Design, vol. 1, pp. 233–318, 1993.

Jai-Tung Huang, et al., "Fluorinated Sugar Analogues of Potential Anti-HIV-1 Nucleosides", J. Med. Chem., 34, pp. 1640–1646, 1991.

Donna M. Huryn and Masami Okabe, "AIDS-Driven Nucleoside Chemistry", Chem. Rev., 92, pp. 1745–1768, 1992.

Bhalchandra V. Joshi and Colin B. Reese, "Some Reactions of (5R)-2-Methylene-5-(thymin-1-yl)-2,5-dihydrofuran", J. Chem. Soc. Perkins Trans. 1, pp. 441–443, 1992.

Bhalchandra V. Joshi, T. Sudhakar Rao and Colin B. Reese, "Conversion of Some Pyrimidine 2'-Deoxyribonucleosides into the Corresponding 2'-, 3'-Didehydro-2', 3'-dideoxynucleosides", J. Chem. Soc. Perkins Trans. I, pp. 2537–2544, 1992.

Muzammil M. Mansuri, et al., "Preparation of 1-(2, 3-Dideoxy-β-D-*glycero*-pent-2-enofuranosyl)thymine (d4T) and 2'-3'-Dideoxyadenosine (ddA): General Methods for the Synthesis of 2'-3'-Olefinic and 2'-3'-Dideoxy Nucleoside Analogues Active against HIV", J. Org. Chem., 54, pp. 4780–4785, 1989.

Morris J. Robins, et al., "A Mild Conversion of Vicinal Diols to Alkenes. Efficient Transformation of Ribonucleosides into 2'-Ene and 2',3'-Dideoxynucleosides", Tetrahedron Letters, vol. 25, No. 4, pp. 367–370, 1984.

Edward E. Knaus et al, "The Synthesis of [$^{36}$Cl]—, [$^{82}$Br]— and [$^{123}$I]–Labelled 1-(3'-Chloro-(Bromo and Iodo)-3'-Deoxy-β-D-arabinofuranosy)uracil," Int. J. Appl. Radiat. Isot., vol. 35, No. 11, pp. 1053–1056, 1984.

Chemical Abstracts, vol. 68, No. 19, May 6, 1968, abstract no. 87502, p. 8452.

Primary Examiner—Gary E. Hollinden
Assistant Examiner—L. Eric Crane
Attorney, Agent, or Firm—Richard P. Ryan

[57] ABSTRACT

The present invention concerns an improved process of making d4T from 5-MU. Another aspect of the invention relates to useful intermediates produced during the process.

13 Claims, No Drawings

PREPARATION OF D4T FROM 5-METHYLURIDINE

BACKGROUND OF THE INVENTION

The compound d4T (2',3'-didehydro-3'-deoxythymidine) is a new antiviral drug approved recently for the treatment of AIDS. It is named Stavudine by the U.S. Adopted Name (USAN) and marketed as ZERIT.™ The current process for producing d4T uses an expensive starting material, thymidine. (For a leading reference see: Joshi, B. V.; Rao, T.; Sudhakar, R.; Reese, C. B., *J. Chem. Soc. Perkin Trans. I*, 1992, 2537.) Alternative approaches to d4T utilize less costly ribonucleoside 5-methyluridine (5-MU). (For reviews see: Huryn, D. M.; Okabe, M., *Chem. Rev.*, 1992, 92, 1745; Dueholm, K. L.; Pedersen, E. B., *Synthesis*, 1992, 1; Herdewijin, P.; Balzarini, J.; De Clercq, E., in *Advances in Antiviral Drug Design*, Vol. 1, De Clercq, E., Ed., JAI Press Inc., Middlesex, England, 1993, p. 233.) For example, zinc reduction of cis-3'α-acetyloxy-2'α-bromo derivative of 5-MU affords d4T product in about 50% yield. (See Mansuri, M. M.; Starrett, J. E., Jr.; Wos, J. A.; Tortolani, D. R.; Brodfuehrer, P. R.; Howell, H. G.; Martin, J. C., *J. Org. Chem.*, 1989, 54, 4780.) However, large amount of thymine by-product also forms via competitive elimination which requires expensive chromatographic separation from the d4T product. Alternative methods of making this antiviral agent are constantly explored in order to find a more economical method of preparing the large-scale amounts of d4T.

The present invention is a new improved synthesis of d4T from 5-methyluridine (1) (Scheme 1). The key step of this invention involves a metal reductive elimination of a mixture of novel trans-3'α-halo-2'β-acyloxy/trans-3'β-acyloxy-2'α-halo derivatives of 5-MU 5a and 5b to give 5'-mesyl-d4T (6). In sharp contrast to the previous zinc reduction of cis-3'α-acetyloxy-2'α-bromo derivative of 5-MU where about 40% of thymine by-product is formed (Mansuri, M. M.; Starrett, J. E., Jr.; Wos, J. A.; Tortolani, D. R.; Brodfuehrer, P. R.; Howell, H. G.; Martin, J. C. *J. Org. Chem.*, 1989, 54, 4780), the zinc reduction of trans-acyloxy halo derivatives of 5-MU 5a and 5b in which X is bromo and R is methyl affords d4T without noticeable thymine by-product contamination.

SUMMARY OF THE INVENTION

The present invention concerns an improved process of making d4T from 5-MU. Another aspect of the invention relates to useful intermediates produced during the process.

DETAILED DESCRIPTION OF THE INVENTION

In the instant application, unless otherwise specified explicitly or in context, the following definitions apply. The numbers in subscript after the symbol "C" define the number of carbon atoms a particular group can contain. For example "$C_{1-6}$ alkyl" refers to straight and branched chain alkyl groups with one to six carbon atoms, and such groups include methyl, ethyl, n-propyl, isopropyl, n-butyl, t-butyl, n-pentyl, n-hexyl, 3-methylpentyl, or the like alkyl groups. "Aryl" means aromatic hydrocarbon having six to ten carbon atoms; examples include phenyl and naphthyl which can optionally be substituted with one to five halogen atoms, $C_{1-6}$ alkyl and/or aryl groups. "Acyl" refers to a radical RCO— in which R is $C_{1-6}$ alkyl. "Halogen," "halide," or "halo" means chlorine, bromine and iodine. Alkali metal refers to metal in Group IA of the periodic table, preferably lithium, sodium and potassium. Alkaline earth metal refers to metal in Group IIA of the periodic table, preferably calcium and magnesium.

The abbreviations used herein are conventional abbreviations widely employed in the art; some of which are:

| | |
|---|---|
| Ms | Methanesulfonyl |
| DMF | N,N-dimethylformamide |

The improved d4T process of this invention is depicted in Scheme I and involves the following chemical reactions:

Step (a): The production of 2',3',5'-tri-O-mesyl-5-methyluridine (2) from 5-MU is described in our copending application U.S. Ser. No. 08/309,637 filed Sep. 23, 1994, which is herein incorporated by reference in its entirety. More specifically, this step involves preferably the use of a polar solvent, such as acetone, and about 3 to 5 equivalents of an organic base that is stronger than pyridine but weaker than triethylamine. Useful organic bases are those such as the picolines, the lutidines, and preferably N-methylmorpholine; in effect, bases with pK values between 5.5 and 8.0. The reaction proceeds at warm temperatures such as room temperature to about 65° C. and is complete usually within about 0.5 to 2.0 hours. Typical reaction conditions appear in Example 1 that follow.

Step (b): Treatment of compound 2 with MOH results in the formulation of 5'-mesyl-2',3'-anhydro-5-methyluridine (3). MOH refers to an alkali metal hydroxide such as potassium hydroxide, sodium hydroxide, and lithium hydroxide. Preferred MOH is sodium hydroxide in about 1N concentration. (A somewhat similar procedure has been previously reported for the preparation of 5'-mesyl-2',3'-anhydrouridine, see: Codington, J. F.; Fecher, R.; Fox, J. J., *J. Org. Chem.*, 1962, 27, 163.)

Steps (c) and (d): The epoxide 3 is then opened with hydrogen halide selected from hydrogen chloride, hydrogen bromide and hydrogen iodide to afford a mixture of regioisomers 4a and 4b. Preferred hydrogen halide is hydrogen bromide which can be generated in situ from acetyl bromide and methanol to afford a mixture of alchohols 4a and 4b in which X is bromo. A mixture of 4a and 4b is then treated with acyl halide to give a mixture of regioisomers 5a and 5b. In this second step, acetyl bromide is preferred which affords trans-bromoacetates.

If one so desires, each regioisomer can be isolated during these steps from a mixture of 4a and 4b, or 5a and 5b, and the following reactions can be carried on each separated regioisomer to eventually afford d4T.

Step (e): The reductive elimination of a mixture of 5a and 5b with a reducing metal, such as zinc, magnesium, zinc-couple such as Zn—Cu, or sodium affords 5'-mesyl-d4T (6). Here the preferred reducing metal is zinc. As stated earlier the advantage of this specific reductive elimination is that it proceeds cleanly in high yield with little or no cleavage of thymine which is difficult to separate from the product. (Compounds 6 is described in Joshi, B. V.; Reese, C. B., *J. Chem. Soc. Perkin Trans. I*, 1992, 441.) (Zinc reduction of trans-acetyloxy bromo derivatives of adenosine (Ia and Ib) have been reported, see: Robins, M. J. et al, *Tetrahedron Lett.*, 1984, 25, 367. However, not only the nucleo base is different from thymine, but the orientations of the acyloxy and halo groups are different from 5a and 5b, e.g. 3'β-bromo-2'α-acetyloxy/3'α-acetyloxy-2'β-bromo vs 3'α-bromo-2'β-acetyloxy/3'β-acetyloxy-2'α-bromo. It is worthwhile to note that when the nucleo base is thymine instead of adenine, analogous compounds to Ia and Ib can not be obtained due to the thymine base participation, see Mansuri, M. M.; Starrett, J. E., Jr.; Wos, J. A.; Tortolani, D. R.; Brodfuehrer, P. R.; Howell, H. G.; Martin, J. C. *J. Org. Chem.*, 1989, 54, 4780.)

5,608,049

3   4

SCHEME 1

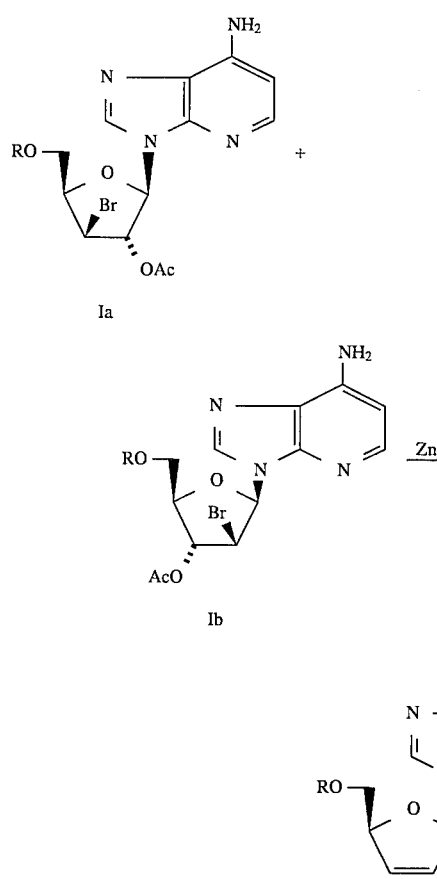

Ia

Ib

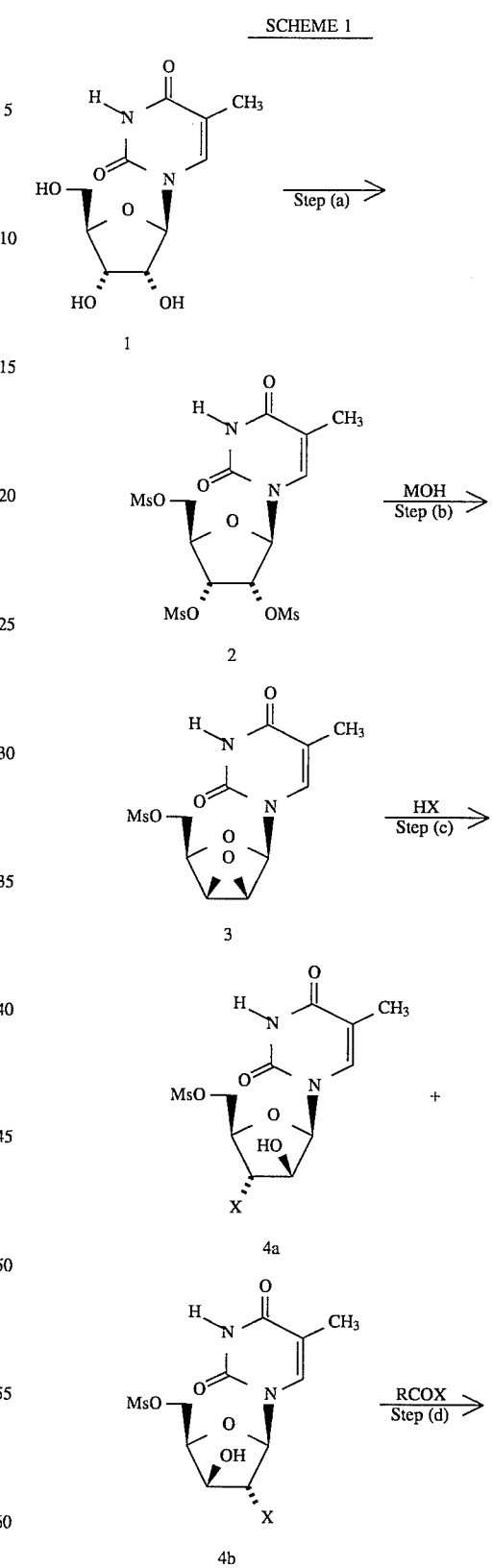

Step (f): Reaction of compound 6 with 1.2 equivalent of R'COOT in a polar solvent such as DMF at an elevated temperature such as at about 100° C. for about 6 hours affords 5'-acyloxy-d4T of formula 7. T is an alkali or alkaline earth metal such as sodium, potassium, lithium, calcium, magnesium, etc., and R' is $C_{1-6}$ alkyl or aryl. Preferred R'COOT is sodium benzoate.

Step (g): The conversion of a compound of formula 7 to d4T can be achieved by many conventional methods known to convert esters to alcohols. Prior art syntheses of d4T generally use sodium methoxide in methanol to achieve the 5'-deprotection. Our copending application U.S. Ser. No. 08/309,637 filed Sep. 23, 1994, which has been incorporated by reference teaches the clean deprotection of benzoyl (or another acyl group) with n-butylamine. Furthermore, the addition of N-methylpyrrolidinone (NMPO) in butyl acetate allows isolation of the d4T.NMPO complex by filtration from the reaction mixture. This isolation via the NMPO solvate effectively eliminates contaminants which are difficult to separate from product, particularly on a large scale. The d4T.NMPO complex can be decomposed by heating in isopropanol to give d4T in high yield and purity.

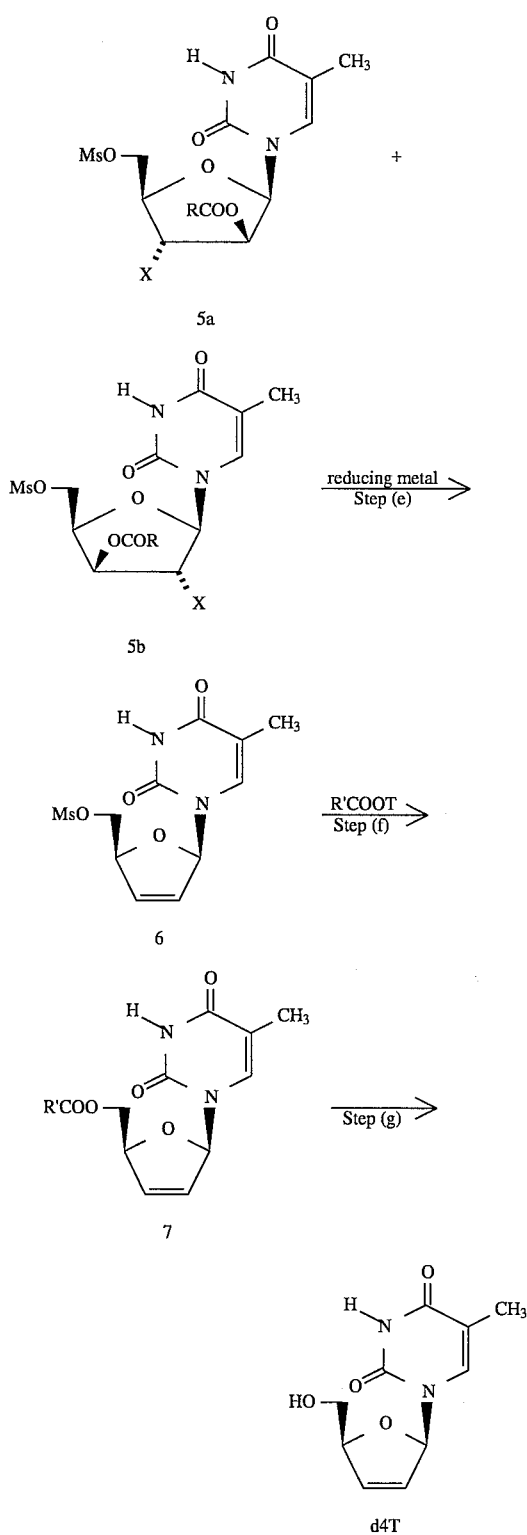

-continued
SCHEME 1

The specific examples that follow illustrate the instant invention, and are not to be construed as limiting the invention in sphere or scope. The methods may be adapted to variations in order to produce the compounds embraced by this invention, and without departing from the spirit of the invention. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone). DMSO-$d_6$ (perdeuterodimethylsulfoxide), $D_2O$ (deuterated water), $CDCl_3$ (deuterochloroform) and other conventional deuterated solvents.

EXAMPLE 1

2',3',5'-Tris(methanesulfonyl)-5-methyluridine (2)

Pyridine Procedure

To a stirred mixture of 5-methyluridine (12.8 g, 50 mmol) in pyridine (75 ml) at 0° C. was added methanesulfonyl chloride (17.4 ml, 225 mmol). The reaction mixture was stirred at 0° C. for five hours then poured into ice-water (500 ml) with stirring. Tris(methanesulfonyl)-5-methyluridine 2 precipitated and the mixture was stirred for 5 min. The solid product was collected by filtration and washed with water (3×200 ml) and dried. Yield 21.6 g, 89%.

$^1$H-NMR (DMSO-$d_6$) $\delta$ 1.77 (s, 3H), 3.24 (s, 3H), 3.34 (s, 3H), 3.36 (s, 3H), 4.47–4.60 (m, 2H), 5.33 (m, 1H), 5.54 (m, 1H), 5.97 (d, J=4.5 Hz, 1H), 7.56 (s, 1H), 11.56 (s, 1H).

N-Methylmorpholine Procedure

N-Methylmorpholine (29.6 mL, 266 mmoles) was added to a slurry of 5-methyluridine hemihydrate (15.64 g, 58.5 mmoles) in acetone (68 mL) and the resulting mixture was cooled to 5° C. A solution of methanesulfonyl chloride (20.1 mL, 255 mmoles) in acetone (30 mL) was added over 45 minutes, causing the reaction temperature to rise to 45°–50° C. After stirring an additional 1.4 hours the N-methylmorpholine hydrochloride was removed by filtration and the cake was washed with acetone (2×30 mL). The combined filtrate and washes were then added to water (1 L) at 10°–15° C. After stirring for 1.1 hours the white precipitate was filtered, washed with water (2×75 mL), and dried under vacuum. Yield 27.95 g (97%).

EXAMPLE 2

5'-Methanesulfonyl-2',3'-anhydro-5-methyluridine (3)

To a solution of 49 ml 1N sodium hydroxide was added 2',3',5'-tris(methanesulfonyl)-5-methyluridine (2, 6.0 g). The mixture was stirred at 70°–72° C. for 15 minutes and then cooled 0° C. The pH was adjusted to 4 by using concentrated HCl. The resulting slurry was filtered, washed with 2×10 ml water and dried to give 5'-methanesulfonyl-2'-3'-anhydro-5-methyluridine (3), 3.1 g, (84%).

$^1$H-NMR (DMSO-$d_6$) $\delta$ 1.79 (s, 3H), 3.22 (s, 3H), 4.10 (m, 2H), 4.38 (m, 2H), 4.55 (m, 1H), 6.15 (s, 1H), 7.49 (s, 1H), 11.48 (s, 1H).

EXAMPLE 3

1β-(5'β-Methanesulfonyl-2'β-hydroxy-3'α-bromofuranosyl)-thymine and 1β-(5'β-Methanesulfonyl-2α-bromo-3'β-hydroxyfuranosyl)-thymine (4a' and 4b')

To a mixture of 5'-methanesulfonyl-2',3'-anhydro-5-methyluridine (3, 2.4 g) in 120 ml of methanol was added acetyl bromide (6.0 ml). The reaction mixture was then refluxed for 7 hours. The solvent was removed to give an oil which was dried under vaccum to give a mixture of compounds 4a' and 4b', 2.9 g (96%).

Ratio of two isomers was 2.53:1. $^1$H-NMR data for the major isomer (DMSO-d$_6$) δ 1.79 (s, 3H), 3.24 (s, 3H), 4.40–4.60 (m, 5H), 6.20 (d, J=6.6 Hz, 1H), 7.38 (s, 1H), 11.38 (s, 1H); 1H-NMR data for the minor isomer (DMSO-d$_6$) δ 1.79 (s, 3H), 1.96 (s, 3H), 3.22 (s, 3H), 4.4–4.7 (m, 5H), 6.18 (d, J=3.8 Hz, 1H), 7.59 (s, 1H), 11.48 (s, 1H).

EXAMPLE 4

1β-(5'β-3-Methanesulfonyl-2'β-acetoxy-3'α-bromofuranosyl)-thymine and 1β-(5'β-Methanesulfonyl-2α-bromo-3'β-3'β-acetoxyfuranosyl)-thymine (5a' and 5b')

To a mixture of the hydroxy bromides 4a' and 4b' (1.2 g) in 20 ml of ethyl acetate was added acetyl bromide (2.0 ml). The reaction was refluxed for 2 hours. After cooling, the reaction mixture was diluted with 40 ml of ethyl acetate, washed with saturated NaHCO$_3$ (2×50 ml), brine (50 ml) and dried over MgSO$_4$. Removal of solvent afforded a mixture of bromo acetates 5a' and 5b', 1.25 g (95%).

Ratio of two isomers was 2.6:1. $^1$H-NMR data for the major isomer (DMSO-d$_6$) δ 1.79 (s, 3H), 1.94 (s, 3H), 3.25 (s, 3H), 4.40–4.70 (m, 4H), 5.62 (t, J=6.8 Hz, 1H), 6.35 (d, J=6.7 Hz, 1H), 7.40 (s, 1H), 11.42 (s, 1H); $^1$H-NMR data for the minor isomer (DMSO-d$_6$) δ 1.79 (s, 3H), 1.96 (s, 3H), 3.24 (s, 3H), 4.40–4.70 (m, 4H), 5.57 (t, J=3.7 Hz, 1H), 6.35 (d, J=3.8 Hz, 1H), 7.49 (s, 1H), 11.48 (s, 1H).

EXAMPLE 5

5'-Methanesulfonyl-2',3'-didehydro-3'-deoxythymidine (6)

To a mixture of 1.0 g of activated zinc dust in 25 ml methanol was added the bromo acetates 5a' and 5b' (1.0 g). The mixture was stirred at room temperature for 1.5 hours. Excess zinc was filtered and washed with 2×10 ml methanol. Removal of solvent afforded 5'-mesyl-d4T (6), 0.60 g (88%).

$^1$H-NMR (DMSO-d$_6$) δ 1.73 (s, 3H), 3.16 (s, 3H), 4.40 (m, 2H), 5.02 (s, 1H), 6.03 (d, J=5.8 Hz, 1H), 6.42 (d, J=5.9 Hz, 1H), 6.84 (m, 1H), 7.27 (s, 1H), 11.39 (s, 1H).

EXAMPLE 6

5'-Benzoyl-2',3'-didehydro-3'-deoxythymidine (7')

To a mixture of 5'-mesyl-d4T (6, 0.4 g) in 6 ml of DMF was added powdered sodium benzoate (0.24 g). The reaction was stirred at 100° C. for 6 hours. After cooling, water (30 ml) was added. The resulting precipitate was filtered, washed with 2×5 ml water and dried to give 5'-benzoly-d4T (7'), 0.04 g (91%).

$^1$H-NMR (DMSO-d$_6$) δ 1.35 (s, 3H), 4.41–4.48 (m, 2H), 5.10 (m, 1H), 6.04 (d, J=5.8 Hz, 1H), 6.53 (d, J=5.8 Hz, 1H), 6.80 (s, 1H), 7.10 (s, 1H), 7.51–7.95 (m, 5H), 11.37 (s, 1H).

EXAMPLE 7

2',3'-Didehydro-3'-deoxythymidine-N-methylpyrrolidinone Complex

To n-butylamine (133 ml) was added 5'-benzoyl-d4T (7', 70.0 g). The reaction was heated at 70° C. for six hours. After cooling to 20°–25° C., N-methylpyrrolidinone (NMPO, 41.3 ml) and n-butyl acetate (350 ml) were added. Excess n-butylamine (~112.4 ml) along with 175 ml of n-butyl acetate was removed via vacuum distillation at 50° C. The resulting slurry was cooled to 20°–25° C. over one hour and stirred for 30 minutes. The slurry was then cooled to −10° to −15° C. and stirred for 1.5 hours. The cake was filtered and washed with 2×50 ml cold (−10° to −15° C.) n-butyl acetate and dried to give d4T.NMPO complex, 59.0 g (85.6%).

EXAMPLE 8

2',3'-Didehydro-3'-deoxythymidine (d4T)

Methoxide Procedure

To a stirred slurry of 5'-benzoyl-d4T (7') (2.4 g, 7.31 mmol) in methanol (24 ml) was added sodium methoxide solution (4.8 mL, 25%, 21 mmol). The resulting solution was stirred at room temperature for 3 hours. The reaction mixture was neutralized with strong acid resin (Dowex 50×8-200, prewashed with methanol) to pH 4. The resin was filtered and the cake was washed with methanol (2×10ml). Removal of methanol gave a wet solid to which methylene chloride (10 ml) was added. The resulting mixture was stirred for 30 min. and then the d4T product was collected by filtration, washed with methylene chloride (2×5 ml) and dried. Yield 1.29 g, 79%.

$^1$H-NMR (DMSO-d$_6$) δ 1.71 (s, 3H), 3.59 (m, 1H), 4.76 (m, 1H), 5.02 (s, 1H), 5.89 (d, J=5.7 Hz, 1H), 6.38 (d, J=5.7 Hz, 1H), 6.80 (s, 1H), 7.63 (s, 1H), 11.27 (s, 1H).

d4T.NMPO Complex Procedure

To 500 ml of isopropanol was added 50.0 g d4T.NMPO, 5.0 g Dicalite, 5.0 g Darco KB. The mixture was heated to reflux and then filtered hot through a bed of Dicalite. The filter cake was rinsed with 150 ml hot isopropanol. The filtrate and rinse were combined and vacuum concentrated to a final volume of 200 ml. The concentrated mixture was heated to reflux to give a solution and then cooled slowly to form product slurry at 50° C. The slurry was then cooled to 0° C. and held for 30 minutes. The cake was filtered, washed with cold (0° C.) isopropanol and dried to give d4T, 30.5 g (87.9%).

What we claim is:

1. A process of producing 2',3'-didehydro-3'-deoxythymidine (d4T) comprising the steps of:

a) treating 2',3',5'-tris(methanesulfonyl)-5-methyluridine (2)

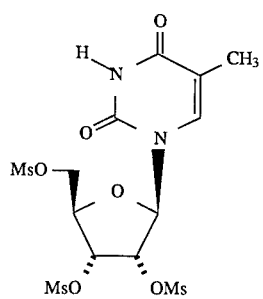

with alkali metal hydroxide to afford epoxide 3

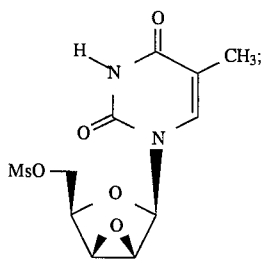

3 b) treating epoxide 3 with hydrogen halide to afford a mixture of compounds 4a and 4b in which X is chloro, bromo or iodo

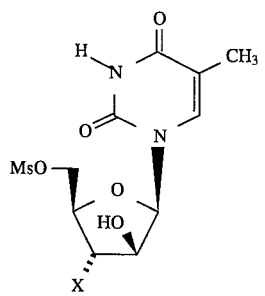

4a

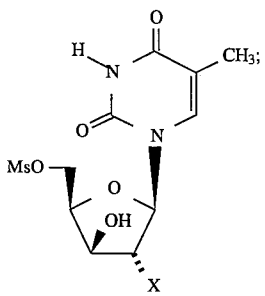

4b c) treating a mixture of 4a and 4b with acyl halide to afford a mixture of 5a and 5b in which R is $C_{1-6}$ alkyl

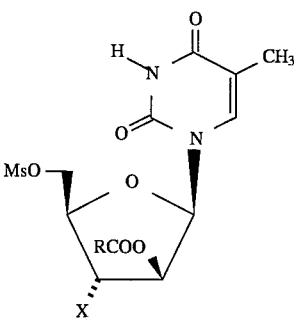

5a

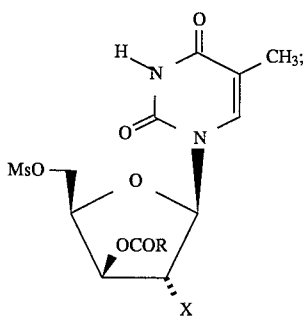

5b d) treating a mixture of 5a and 5b with reducing metal to afford compound 6

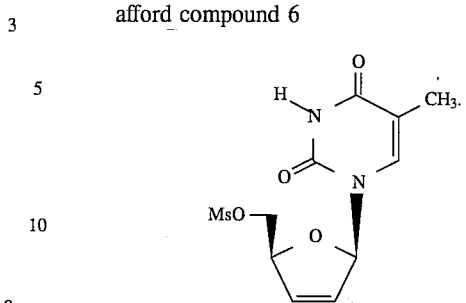

6

2. The process of claim 1 in which alkali metal hydroxide of step (a) is sodium hydroxide.

3. The process of claim 1 in which hydrogen halide of step (b) is hydrogen bromide.

4. The process of claim 1 in which acyl halide of step (c) is acetyl bromide.

5. The process of claim 1 in which reducing metal of step (d) is zinc.

6. A process of producing 2',3'-didehydro-3'-deoxythymidine (d4T) comprising, reacting a compound of 5a or 5b, or a mixture thereof with a metal reducing agent

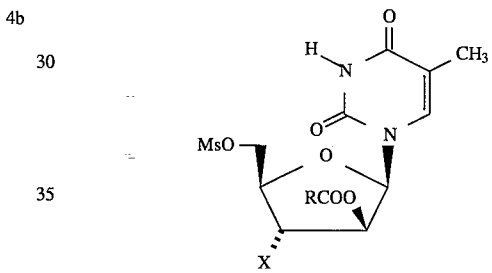

5a

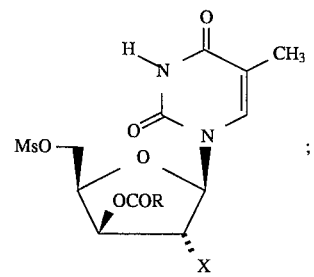

5b in which X is chloro, bromo or iodo; and R is $C_{1-6}$ alkyl; to afford compound of formula 6

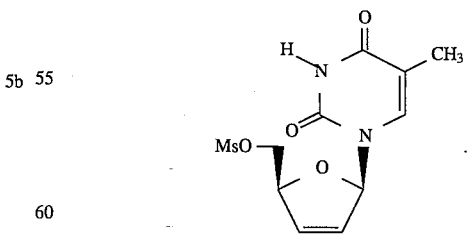

6

7. The process as claimed in claim 6 in which R is methyl, X is bromo, and metal reducing agent is zinc.

8. A compound of formula 4a or 4b, or a mixture thereof

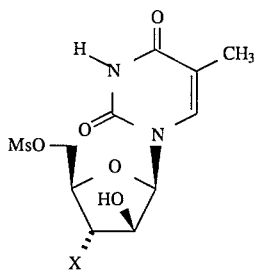

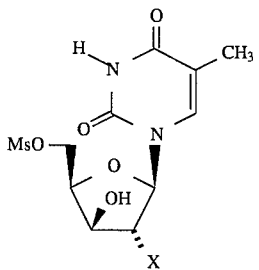

in which X is chloro, bromo or iodo.

9. A compound or a mixture of claim 8 in which X is bromo.

10. A compound of formula 5a or 5b, or a mixture thereof

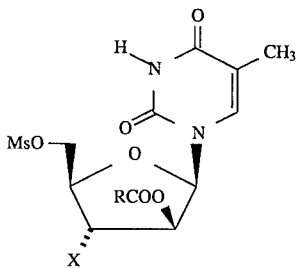

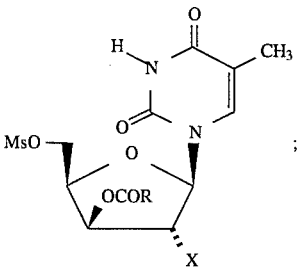

in which X is chloro, bromo or iodo; and R is $C_{1-6}$ alkyl.

11. A compound or a mixture of claim 10 in which X is bromo, and R is methyl.

12. A process of producing 2',3'-didehydro-3'-deoxythymidine (d4T) comprising the steps of:

a) treating 2',3',5'-tris(methanesulfonyl)-5-methyluridine (2)

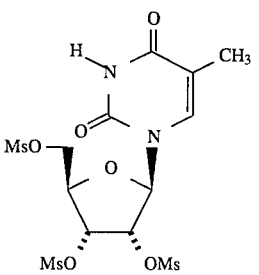

with alkali metal hydroxide to afford epoxide 3

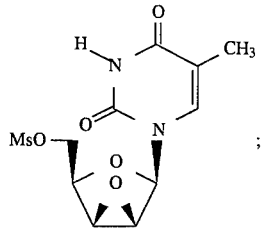

b) treating epoxide 3 with hydrogen halide to afford a mixture of compounds 4a and 4b in which X is chloro, bromo or iodo

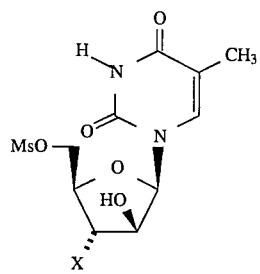

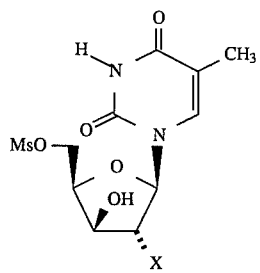

c) treating a mixture of 4a and 4b with acyl halide to afford a mixture of 5a and 5b in which R is $C_{1-6}$ alkyl

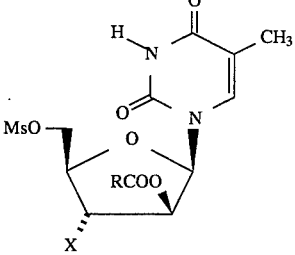

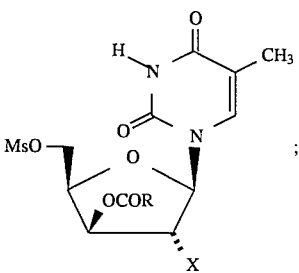

d) treating a mixture of 5a and 5b with reducing metal to afford compound 6

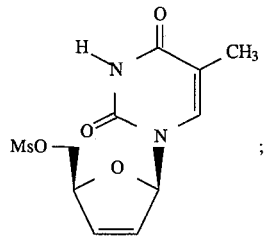

6

(e) reacting compound 6 with R'COOT, in which T is alkali or alkaline earth metal selected from sodium, potassium, lithium, calcium or magnesium; and R' is aryl or $C_{1-6}$ alkyl; to afford a compound of formula 7

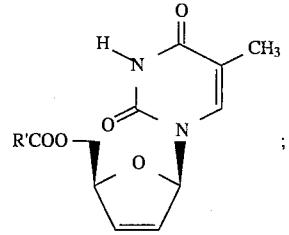

7

(f) converting R'COO— radical in a compound of formula 7 to hydroxy by using $C_{1-6}$ alkylamine.

13. The process of claim 12 in which alkali metal hydroxide of step (a) is sodium hydroxide; hydrogen halide of step (b) is hydrogen bromide; acyl halide of step (c) is acetyl bromide; reducing metal of step (d) is zinc; R'COOT of step (e) is sodium benzoate; and $C_{1-6}$ alkylamine of step (f) is n-butylamine.

* * * * *